(12) United States Patent
Hughes

(10) Patent No.: US 6,589,248 B1
(45) Date of Patent: Jul. 8, 2003

(54) PATELLAR ALIGNMENT DEVICE

(76) Inventor: Joe L. Hughes, 4981 Lake Fjord Pass, Marietta, GA (US) 30068

( * ) Notice: Subject to any disclaimer, the term of this patent is extended or adjusted under 35 U.S.C. 154(b) by 0 days.

(21) Appl. No.: 10/060,077

(22) Filed: Jan. 29, 2002

(51) Int. Cl.[7] .............................. A61B 17/58; A61F 2/00; A61F 2/32; A61F 2/38
(52) U.S. Cl. ........................... 606/102; 606/88; 606/89; 606/99; 623/20.14; 623/20.15; 623/20.18; 623/20.2
(58) Field of Search ........................ 606/86, 88, 89, 606/91, 99, 102, 53; 623/18.11, 20.14, 20.15, 20.18, 20.2, 908

(56) References Cited

U.S. PATENT DOCUMENTS

| | | | |
|---|---|---|---|
| 5,776,200 A | * | 7/1998 | Johnson et al. ................ 623/20 |
| 6,315,798 B1 | * | 11/2001 | Ashby et al. ............. 623/20.17 |
| 2002/0128719 A1 | * | 9/2002 | Burkinshaw ................ 623/20.2 |

* cited by examiner

*Primary Examiner*—Pedro Philogene
*Assistant Examiner*—Anuradha Ramana
(74) *Attorney, Agent, or Firm*—Kent R. Moore

(57) ABSTRACT

A patellar alignment device for determining the position of a patella prosthesis. The device comprises two components—a baseplate and a mobile component which is preferably magnetically attached to the baseplate. During a surgical procedure to replace the knee, the baseplate is temporarily attached to the back of the patella. The baseplate may contain spikes or prongs to secure it to the patella. The baseplate further includes a series of slots for marking the patella. The mobile component resembles a patella and is placed on the baseplate. The patella with the alignment device in place is then placed in position on the knee and trialed. Because the mobile component is free to move on the baseplate, it finds the position that is most amenable to a natural knee movement. The alignment device is then exposed and the patella is marked at the position of the mobile component. Since the baseplate contains a series of slots, the patella can be easily marked at several locations around the mobile component. The entire patella alignment assembly is then removed and the final prosthetic device can be inserted at the marked location.

10 Claims, 3 Drawing Sheets

PATELLAR ALIGNMENT DEVICE

1. BACKGROUND

For a variety of reasons, whether from the natural aging process or from an injury, the knee may become damaged to such an extent that it needs to be completely repaired—usually through a surgical procedure called a total knee arthroplasty. In an arthroplasty, the damaged portions of the knee are removed and replaced with prosthetic components that are the size and shape of the original undamaged portions of the knee. It is important that the replacement prosthetics be aligned properly to prevent unnecessary wear and tear on the new components and to prevent complications from occurring due to the misalignment. To assist with the proper alignment of the prosthetic replacements, trial components are first installed during surgery. The trial components are the size and shape of the final components but are only used to test the alignment and fit of the knee before installing the permanent components.

There are three primary bones that comprise a knee joint in a human that are the subject of an arthroplasty—the lower portion of the femur (the thigh bone), the upper portion of the tibia (the shin) and the patella (the knee cap). The knee cap is connected both to the femur and to the tibia by a series of ligaments and tendons. The femur has a groove or sulcus for the patella to glide in as the knee is flexed. The tendons and ligaments not only help hold the patella in place but also assist in maintaining its proper position in the groove.

As part of the arthroplasty, the surgeon removes the lower portion of the femur, the upper portion of the tibia, and the posterior portion of the patella. Once the areas have been removed sufficiently to clear away any damage, trial components are inserted and the knee joint is tested for proper alignment by flexing and extending the knee. Any misalignment is corrected prior to permanently attaching the final components. The pain, stiffness, swelling, and deformity from walking and weight-bearing on this knee is then eliminated.

To perform the surgery, the knee is opened by an anterior incision and dissection carried down to the joint surfaces. The femur's surface is removed by the use of jigs for sawing the femur at the proper location to remove the damaged area. Similarly, the tibia is then exposed and it's damaged surfaces removed by using jigs for cutting the surfaces correctly. Trial components, usually made of plastic, are inserted temporarily at the removed sections of the femur and tibia and are used to check the alignment and fitting of the knee with its new components.

Once the femur and tibia have been fitted with the trial components, attention is directed to the patella. The procedure for repairing the patella varies depending on the surgeon. Some surgeons do not replace the back surface of the patella and leave it as it is. However, most surgeons replace the back surface of the patella. This is done by first measuring and removing the back 7–10 mm of bone and cartilage from the patella. Traditionally, a hole is the drilled in the center or near the center of this area and a trial patella component applied. However, there are some patella prosthesis designs that either require more than one hole or require a recessed area for acceptance of the final component. Existing trial patella components are usually dome-shaped, about the size of a quarter, and have a central stalk on the back side. This stalk or protrusion on the back holds the trial component in place on the back of the cut patella. Traditionally, the trial patella component is inserted and, with the trial femoral and tibial components in place, the knee is flexed and extended and the fitting and alignment of the entire knee is checked, particularly the tracking of the patella along the groove of the lower femoral replacement component.

Existing trial patellas are essentially immobile once they are placed since they are inserted with the stalk or protrusion into the drilled hole. Therefore, if the surgeon drills the hole for mounting the trial patella prosthesis in the drilled proposed location on the back of the patella, then the patella prosthesis will not track properly and additional surgical procedures are necessary to cause the patella to track properly.

In some cases the patella tries to slip out of the groove slightly or subluxate. In others the patella prosthesis may be so poorly aligned that it may move completely out of the groove or dislocate. Existing methods for correcting this misalignment often include a soft tissue release which involves cutting tendons and/or the musculature that holds the patella. Other methods include transferring the tibial tubercle or rotating the femoral or tibial components. Attempts are usually made at accurately placing the trial patella to prevent the necessity of a tissue release, since a tissue release usually causes more bleeding, scarring and difficult rehabilitation after surgery. Additionally, a misaligned patella may cause excessive wear on the prosthetic components of the knee joint, which may reduce the life of the knee joint and necessitate additional surgery.

After the trials are completed, all necessary releases are performed and the positions and alignment acceptable, the final components are inserted and either cemented or press-fit into position. Final trial is performed and the knee is closed.

Many post-operative complications in total knee arthroplasties have been attributed to poor patellar tracking. Dislocations, subluxations, excessive polyethylene wear and particulate debris are some of these complications. It is felt tracking can be improved with better component positioning and alignment at the initial surgery.

Presently, the placement of the patella component on the sectioned patella surface consists of centering the patella component, making certain it fits the whole surface of the patella without overlap. A hole the size of the stalk on the trial component is drilled in the center of the patella and the prosthetic trial inserted. The patella is then placed into its position on the knee joint and trialed to check the tracking on the other components. If it subluxates or dislocates, then a lateral release, patellar tendon transfer, quadriceps snip, or whatever the surgeon chooses is done to allow good tracking. A lateral release is the most common technique used and perhaps the safest. However, a lateral release may be problematic itself since it is believed to reduce the circulation to the patella and could encourage fractures, aseptic necrosis, and/or loosening of the patella component. Also, post-operative rehabilitation is much more difficult as there is more bleeding and scarring post-operatively.

Existing devices and methods for placement of the prosthesis do not consistently allow for propel placement of the final patella prosthesis. Proper placement of the patella component would eliminate the need for additional surgical procedures and the complications associated with those procedures solely to allow the patella to track properly and provide a better performing prosthetic knee joint.

2. SUMMARY

The present invention is a self-aligning patella trial device which allows the surgeon to accurately locate the proper position for the final patella prosthesis. The present patella trial device further eliminates the need to perform additional surgical procedures to allow proper tracking of the device. The trial device of the present invention comprises two components. One of the components is a baseplate for attaching to the posterior portion of the patella. The baseplate is a flat circular plate having a series of slots, preferably radially oriented, in the plate, which may or may not be used during the trial procedure. One side of the flat plate contains small spikes for temporary attachment to the posterior portion of the patella.

The second component resembles the final prosthetic patella and is dome-shaped with a flat surface for placement on the baseplate. The flat surface of the dome-shaped component may be smaller, larger, or equal in diameter to the baseplate. Magnetic plastic materials are now available and could be used to make the components of the present invention.

The two components are preferably made of metal and can be removably attached to each other by means of magnets located on one or the other component. The two components also could be made of plastic or other suitable material usable in a surgical situation. However, a magnetic attachment is the most preferred since it allows the second component to move freely on the baseplate.

When the patella is prepared in surgery, the baseplate of the present invention is placed in position on the back of the patella and temporarily secured to the patella by tapping, clamping or squeezing the baseplate to drive the spikes into the patella and seat the baseplate. In contrast to the existing methods, there is no need to drill a large hole to place the present baseplate. The dome-shaped component is placed on top of the baseplate and secured by means of the magnets. The magnetic attachment allows the dome-shaped component to move on the baseplate without becoming separated from it. Prongs or other supporting spikes at the periphery of the baseplate also help to hold the dome-shaped component in place.

The patella is placed in its position on the knee and the knee joint is flexed and extended. The dome-shaped component then moves to the "path of least resistance" on the baseplate and thereby identifies the natural position or the most comfortable position for the patella prosthesis. The patella is then marked along the perimeter of the dome-shaped component through the radial slots in the baseplate. If the dome-shaped component happens to extend beyond the baseplate edge, the periphery of the dome-shaped component would then be used as a guide for the marks. The base plate and the dome-shaped component are removed and the correct position of the final prosthesis is indicated on the posterior portion of the patella. The final component is then placed on the marked location of the patella.

The immobility of the presently used trial patella component will not allow the patella to move to the most ideal position for the unrestricted smooth gliding action that is needed for a well performing knee joint. The trial component proposed here would allow identification of the position ideal for each specific knee. A movement of the patella trial of as little as 1 mm may be all that is required to give a smooth gliding action. Preferably, the present device perhaps obviate the need for a release. If there is pressure on the knee cap or patella prosthesis from misalignment it causes pain and increased wear on the prosthesis thereby reducing the life of the prosthesis.

The device preferably is made of stainless steel with a magnet (or magnets) for the movable component. The prototypes are made of steel that has been milled. The magnets are inserted in the surface by cutting a hole (or holes) and inserting a magnet of the same size which is held in place by epoxy, or other adhesive, pressure or other method of fixation. There is also the possibility of making the device of ceramic or plastic and using sliding grooves for the moving component. The components could possibly also be made of brass or some other metal such as titanium. The magnets may also be made from some newer materials such as magnetic plastic.

3. DESCRIPTION OF THE DRAWINGS

4. DETAILED DESCRIPTION

Figure 1:
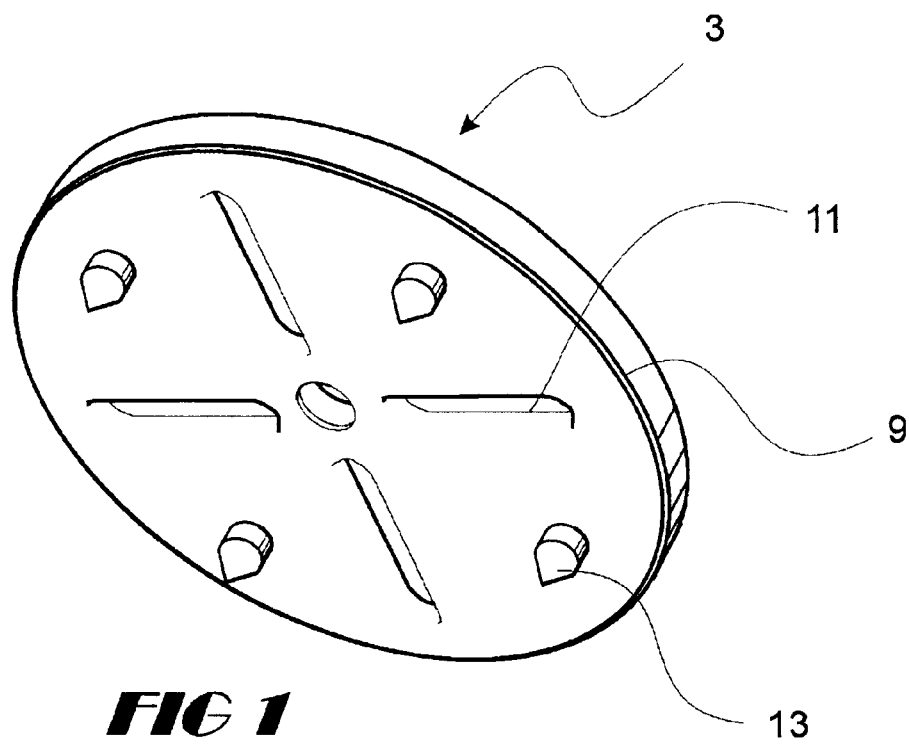
FIG. 1 is a perspective view of a preferred baseplate of the present invention.
Figure 2:
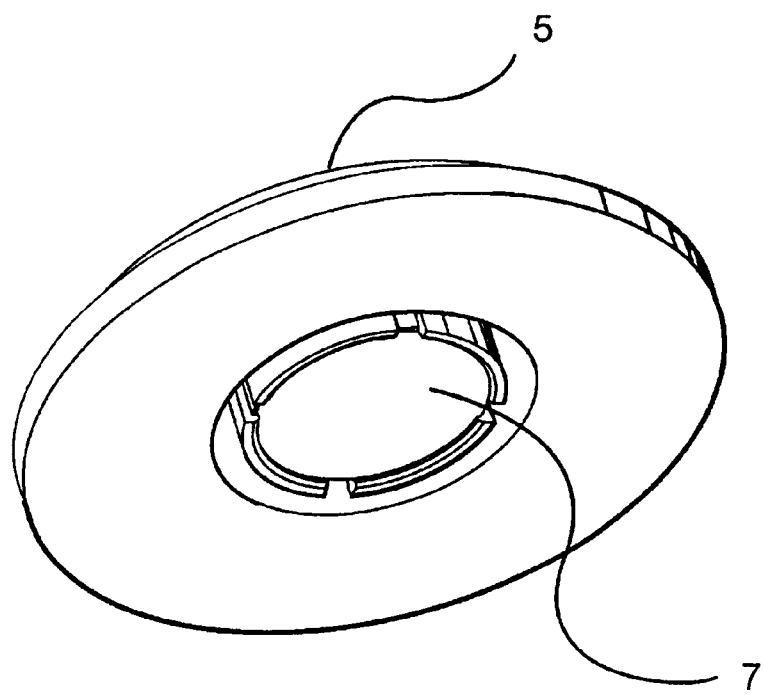
FIG. 2 is a perspective view of a preferred mobile component of the present invention.
Figure 3:
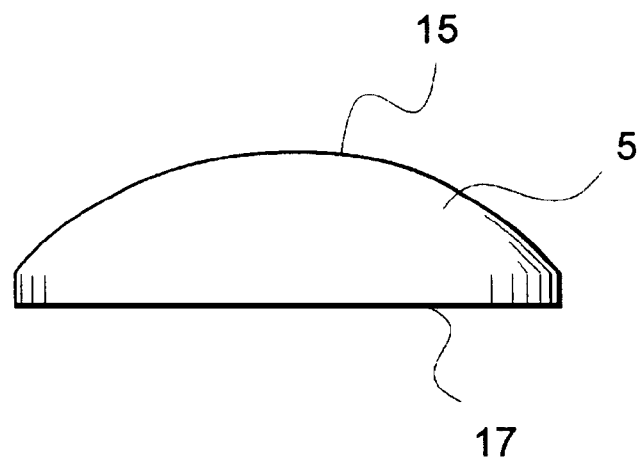
FIG. 3 is a side view of the baseplate shown in FIG. 2.
Figure 4:
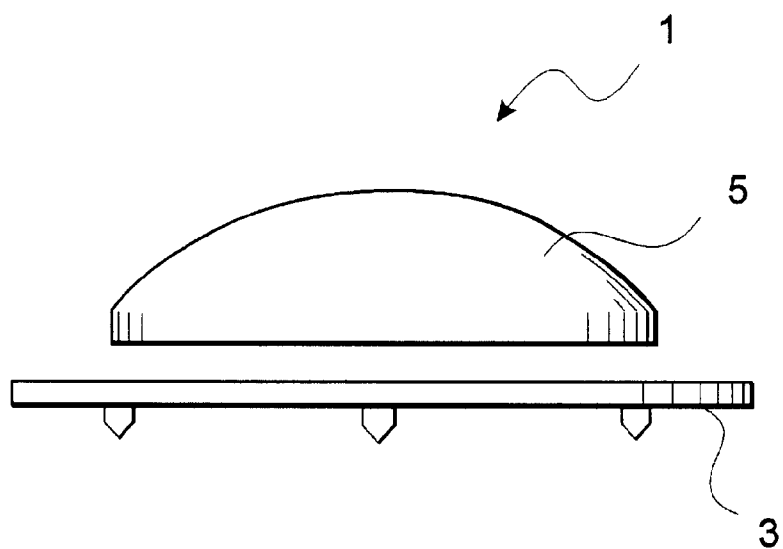
FIG. 4 is a side view of a preferred embodiment of the present invention.

Referring now to FIGS. 1–4, a preferred embodiment of the present patellar alignment device 1 is shown. As indicated in the drawings, the self-aligning patella trial device 1 of the present invention comprises a baseplate 3 for attaching to the posterior portion of a patella (not shown) and a mobile component 5 which is removably attached to the baseplate 3 preferably by magnets 7.

Figure 5:
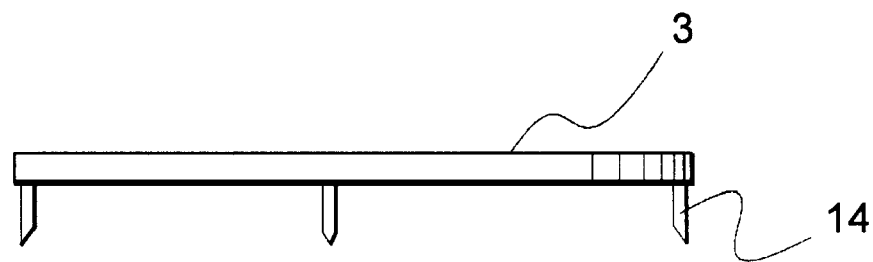
FIG. 5 is a side view of an alternate embodiment of the baseplate of the present invention.

The baseplate 3 preferably is a flat circular plate 9 having slots 11, preferably radially oriented, in the baseplate 3. The slots 11 allow a surgeon to mark the patella during the knee surgery for proper placement of the final prosthetic device. One side of the flat plate 9 contains small spikes 13 for temporary attachment to the posterior portion of the patella. As shown in FIG. 5, outside prongs 14 may be used for added support and positioning of the baseplate 3. However, any suitable means may be used for attaching the baseplate 3 to the patella for purposes of performing the trial, such as screws, springs, clamps, glue or adhesive, or sutures. Such means are well known in the art and need not be discussed here.

The mobile component 5 has a dome-shaped surface 15 on one side to resemble the final prosthetic patella. The dome-shaped surface 15 is the portion of the patellar alignment device that will track in the sulcus of the femur. The mobile component 5 also has a flat surface 17 for placement on the baseplate 3. The flat surface 17 of the mobile component 5 may be of any suitable size relative to the baseplate 3. However, the flat surface 17 of the mobile component 5 preferably is smaller in diameter than the baseplate 3 so that the edges of the baseplate 3 as well as the radial slots 11 extend beyond the perimeter of the mobile component 5 when placed on the baseplate 3.

The two components are preferably made of metal and can be removably attached to each other by means of magnets located on one or the other component. The two components also could be made of plastic or other suitable material usable in a surgical situation. Removable attachment of the components could also be with slots, sutures, rubber, or wire, again giving consideration to the necessity of using components that are suitable for surgery. However, a magnetic attachment is the particularly preferred embodiment since it allows the second component to move freely on the baseplate. In a particularly preferred embodiment, one or both of the components can be made from state of the art plastic materials that have magnetic properties to achieve the magnetic attachment desired.

Figure 6:
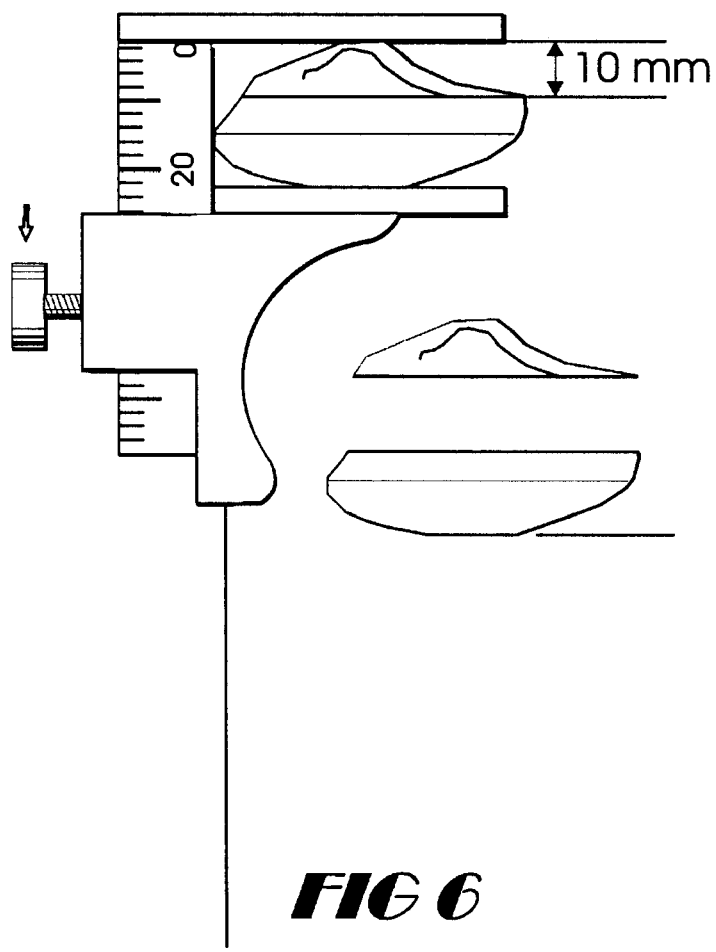
FIG. 6 is a side view of a procedure for measuring the patella.

To prepare the patella in surgery, the patella is actually turned over from its normal position so the surgeon can gain access to the back portion of the patella. As shown in FIG. 6, about 10 mm from the back portion of the patella is measured and marked. Next the marked 10 mm of the back portion of the patella is carefully resected with an oscillating saw.

After the patella is prepared in surgery, the baseplate 3 of the present invention is placed in position on the back of the patella and temporarily secured to the patella by tapping, clamping or squeezing the baseplate 3 to drive the spikes 13 into the patella and seat the baseplate 3. The prongs 14 pass into the soft tissue and along the edge of the bone of the patella. In contrast to the existing methods, there is no need to drill a large hole to place the present baseplate 3.

The mobile component 5 is placed on top of the baseplate 3 and secured by means of the magnets 7. As testing in a surgical situation has indicated, the magnetic attachment allows the mobile component 5 to move on the baseplate 3 without becoming separated from it.

The patella is flipped back over and placed in its position on the knee and the knee joint is flexed and extended. The mobile component 5 then moves to the "path of least resistance" on the baseplate 3 and thereby identifies the natural position or the most comfortable position for the patella prosthesis. The patella is then marked along the perimeter of the mobile component 5 through the radial slots 11 in the baseplate 3 or around the periphery of the mobile component 5. The base plate 3 and the mobile component 5 are removed. The correct position for the final prosthesis is indicated on the posterior portion of the patella by the marks. The final component is then placed on the marked location of the patella.

I claim:

1. A patellar alignment device for proper placement of a patella prosthesis in a knee joint during surgery, the knee joint comprising the lower end of a femur and including a sulcus, the patellar alignment device comprising:

a. a baseplate for attaching to the posterior portion of a patella, said baseplate having a first attachment means for removably attaching the baseplate to the posterior portion of the patella, and said base plate defining one or more openings for placing alignment marks on the posterior portion of the patella; and b. a mobile component removably attached to the baseplate for tracking in the sulcus of the femur.

2. The patellar alignment device of claim 1 wherein the baseplate is substantially circular in shape.

3. The patellar alignment device of claim 1 wherein the baseplate comprises a material having magnetic properties.

4. The patellar alignment device of claim 1 wherein the first attachment means of the baseplate comprises one or more spikes extending from the baseplate, said spikes having sufficient length to penetrate the surface of the patella.

5. The patellar alignment device of claim 1 wherein the attachment means of the baseplate comprises one or more prongs located at the edge of the baseplate.

6. The patella alignment device of claim 1 wherein the one or more openings are radially oriented.

7. The patellar alignment device of claim 6 wherein the baseplate comprises four radially oriented slots.

8. The patellar alignment device of claim 1 wherein the mobile component includes a dome-shaped portion.

9. A patellar alignment device for correcting the alignment of a patella during surgery comprising:

a. a baseplate for attaching to the posterior portion of a patella, said baseplate being removably attached to the posterior portion of the patella, and said base plate defining one or more radially oriented openings for placing alignment marks on the posterior portion of the patella; and b. mobile component removably attached to the baseplate.

10. The patellar alignment device of claim 9 wherein the mobile component is removably attached to the baseplate by magnetic material.

* * * * *